US012766020B2

(12) United States Patent
Schiller et al.

(10) Patent No.: US 12,766,020 B2

(45) Date of Patent: Oct. 20, 2026

(54) DEVICE FOR ESTABLISHING A FORM-FITTING AND/OR FORCE-FITTING CONNECTION TO AN OBJECT, AND ORTHOTIC SYSTEM

(71) Applicant: macu4 AG, Zurich (CH)

(72) Inventors: Lukas Martin Schiller, Zurich (CH); Alec Corentin Chevrot, Chavannes-près-Renens (CH)

(73) Assignee: MACU4 AG, Zurich (CH)

( * ) Notice: Subject to any disclaimer, the term of this patent is extended or adjusted under 35 U.S.C. 154(b) by 132 days.

(21) Appl. No.: 18/821,163

(22) Filed: Aug. 30, 2024

(65) Prior Publication Data

US 2026/0060829 A1 Mar. 5, 2026

(51) Int. Cl.

*A61F 4/00* (2006.01)
*A61F 5/37* (2006.01)
*F16M 13/04* (2006.01)

(52) U.S. Cl.

CPC .............. *A61F 4/00* (2013.01); *A61F 5/3761* (2013.01); *F16M 13/04* (2013.01)

(58) Field of Classification Search

CPC .... A61F 5/3761; A61F 5/3769; A61F 5/3776; A61F 5/3792; A61G 1/04; A61G 1/044; A61G 1/048; A61G 1/052; A61G 5/125; A61G 5/127

See application file for complete search history.

(56) References Cited

U.S. PATENT DOCUMENTS 3,027,895 A * 4/1962 Williams .............. A61F 5/3761 128/878
3,942,194 A 3/1976 Winter
4,549,540 A * 10/1985 Caspari ................. A61F 5/3761 128/882
5,546,962 A * 8/1996 Power ................... A61F 5/3761 128/869

(Continued)

FOREIGN PATENT DOCUMENTS

JP 6526691 B2 6/2019

OTHER PUBLICATIONS

EPO, Extended European Search Report re European Patent Application No. 24162063.2, Jul. 17, 2024.

(Continued)

*Primary Examiner* — Kari K Rodriquez
(74) *Attorney, Agent, or Firm* — Perry + Currier

(57) ABSTRACT

Device for establishing a form/force-fitting connection to an object comprising a limb connection system designed to achieve a mechanical attachment to a limb and a mechanical holding mount in which the object can be positioned. A belt mechanically connected to the holding mount is configured to be partially wrapped around the object in the mechanical holding mount to fix the object in a translational degree of freedom. The device comprises a first mounting element connected to the end section of the belt, having an undercut with a hook element open to a direction of a component of a tensile load transferred from the belt into the first mounting element, and a second mounting element complementary to the undercut. The first mounting element can be fixed along the direction of the tensile load by the undercut, enabling the transmission of tensile load from the belt to the device.

15 Claims, 8 Drawing Sheets

(56) References Cited

U.S. PATENT DOCUMENTS

Figure 1:
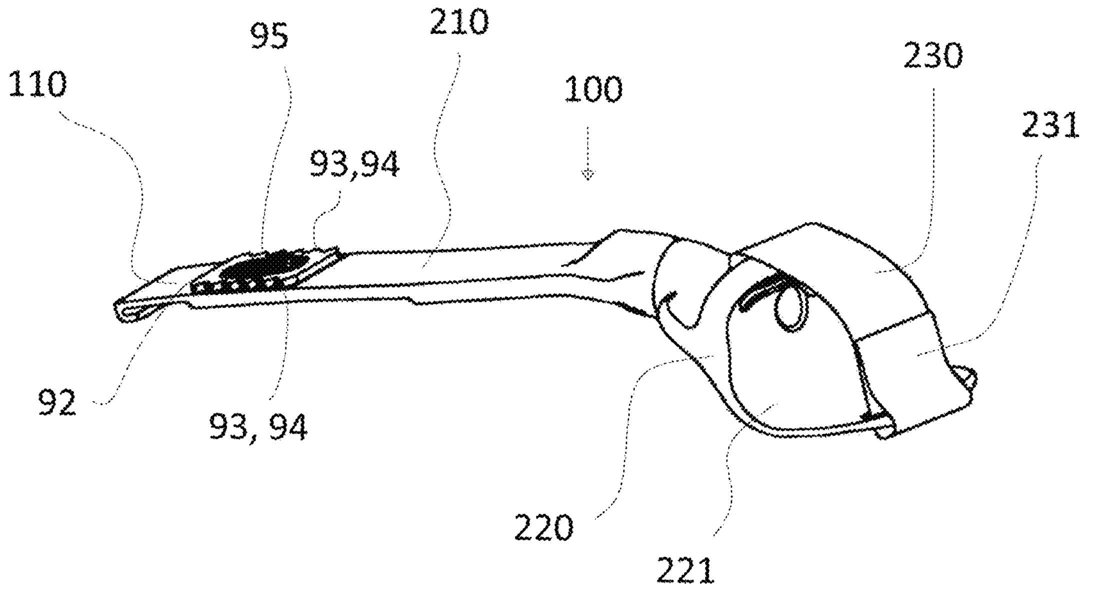

| | | | | |
|---|---|---|---|---|
| 7,513,881 | B1 | 4/2009 | Grim et al. | |
| 8,062,241 | B2 | 11/2011 | Bonutti | |
| 8,425,440 | B2 * | 4/2013 | DeToro | A61F 5/0127<br>602/23 |
| 9,408,738 | B2 | 8/2016 | Boraas et al. | |
| 9,757,266 | B2 | 9/2017 | Hoffman et al. | |
| 9,956,093 | B1 | 5/2018 | Harris | |
| 10,952,887 | B2 | 3/2021 | Le | |
| 11,471,317 | B1 * | 10/2022 | Spears | A61G 7/0507 |
| 2004/0089311 | A1 * | 5/2004 | Graupner | B62B 3/1452<br>128/882 |
| 2009/0099562 | A1 | 4/2009 | Ingimudarson et al. | |
| 2016/0346147 | A1 * | 12/2016 | Brown | A61F 5/3769 |
| 2019/0091043 | A1 | 3/2019 | Pawlik et al. | |
| 2020/0206010 | A1 | 7/2020 | Du et al. | |
| 2021/0219662 | A1 | 7/2021 | Walker | |

OTHER PUBLICATIONS

EPO, Extended European Search Report re European Patent Application No. 24162058.2, Jul. 18, 2024.

EPO, Extended European Search Report re European Patent Application No. 24162105.1, Jul. 29, 2024.

* cited by examiner

DEVICE FOR ESTABLISHING A FORM-FITTING AND/OR FORCE-FITTING CONNECTION TO AN OBJECT, AND ORTHOTIC SYSTEM

The present invention relates to a device for establishing a form-fitting and/or force-fitting connection to an object as well as to an orthotic system, comprising the device.

BACKGROUND

In the case of a congenital deformity or amputation, it may be difficult to perform bimanual activities such as fitness training or kayaking. Similarly, holding a shopping bag or walking on crutches can become a challenge. Daily life for these people is full of little challenges that an ordinary person would never suspect, let alone imagine. People with a birth defect learn to live with it, but outside help is welcome to ease the effort and mental burden. For people who have suffered an amputation as a result of an accident, for example, it is necessary to put a relearning of skills in place. Tools can facilitate not only their daily life but also their rehabilitation. Similarly, in the event of an accident, surgery or injury, hands may become weakened, sensitive, immobilized for a limited period. Therefore, a rapid provision of support is essential to enable affected individuals to continue their activities and daily routines.

Especially if a person has a double disability and is dependent on crutches, any hand restriction can lead to a complete loss of mobility, as the person cannot use conventional crutches without their hands.

SUMMARY

An orthotic system is designed for individuals with partial or complete loss of hand function. This loss may be due to temporary or permanent weakening, hand injury, paralysis, neuromuscular disease, partial absence of the hand or absence due to wrist disarticulation.

An orthotic system designed for forearms is intended to assist individuals with a disability below the wrist. This encompasses various scenarios, including those with only a portion of the palm remaining, small residual fingers, a limited number of fingers, or limited and painful movement capacity. In consequence, the orthotic system should be engineered to hold handles, bars, rods or similar structures and to transmit a tensile or compressive load from the object to the forearm. Furthermore, the orthotic system should enable the use of different types of crutches.

Existing solutions are often poorly adapted, expensive and restricting in terms of the activities they support.

The problem to be solved by the present invention is to provide a device and an orthotic system that ensure comfort through a lightweight, intuitive design while effectively transferring load forces from and/or to a body of a user.

This problem is solved by the subject-matter of the independent claims.

Embodiments of the invention are claimed in dependent claims.

A first aspect of the invention relates to a device for establishing a form-fitting and/or force-fitting connection to an object, comprising at least one limb connection system designed to achieve a mechanical attachment to a limb of a person, for instance to a limb of a person with manual impairment, as well as a mechanical holding mount in which the object can be positioned, such that load transfer from the object to the limb is enabled. Moreover at least one belt is mechanically connected to said holding mount, wherein the belt is configured to be partially wrapped around the object positioned in the mechanical holding mount in order to fix the object in at least one translational degree of freedom. The mechanical attachment to a limb of a person can be a permanent mechanical connection to the limb or a removable mechanical connection. It can be indirectly connected through any limb accessory. The limb of a person can be the forearm or arm of a person. The belt can also be referred to as a strap.

The mechanical holding mount can have a cavity design. The object to which the device can establish a connection may be a handle, bar, rod or similar structure. By connecting the mechanical holding mount for example to a handle of a crutch or any walking assistance apparatus the device works as a walking support module. The device is meant to apply or transfer load to the object or from the object. For example, it can involve the load of leaning body weight onto the crutch or the load of lifting the crutch.

The load can be a tensile or compressive load while pushing or pulling the object. In case of leaning onto the crutch, the load can be carried and transmitted by means of a limb accessory connection from the forearm to the accessory, then by means of the limb connection system from the accessory to the device and by means of the mechanical holding mount from the device to the crutch. In the case of reverse load transmission, the belt can also absorb a part of the load and transmit it to the device.

Fixing the object in at least one translational degree of freedom can mean securing the object or limiting its movement in at least one translational degree of freedom.

The object can be loosely secured in the mechanical holding mount or held under tension. For example, if the belt is loosely wrapped around the object, it can prevent the object from falling out in at least one direction. In this case, there is a form-fitting connection, blocking two translational degrees of freedom.

In some situations, such as when only a compressive load is to be transmitted from the device to the object, there is no need for a tightly fastened belt.

If, however, the belt is tightly wrapped around the object and thus exerting a force on the object, then there is a force-fitting connection, blocking also the third translational degree of freedom. Additionally, the mechanical holding mount can have a flexible, deformable design and thus exert a force on the object when deformed by the geometry of the object, which contributes to the force-fitting connection.

There can be mixed forms of form- and force-fitting connections.

The belt can be directly or indirectly connected to the mechanical holding mount. The belt does not have to be attached to the mechanical holding mount, but can also be connected to any another part of the device and, for example, just be guided along the cavity of the mechanical holding mount.

In one embodiment of the device the limb connection system comprises an insertion element, which is designed to be pushed along a slide-in direction into a retainer attached to a limb, wherein the insertion element has a transversal extension and a longitudinal extension longer than the transversal extension and can be inserted along its longitudinal extension into the retainer such that at least one translational degree of freedom perpendicular to the slide-in direction of the insertion element is blocked or can be blocked by the retainer.

The retainer can be part of a limb accessory which is or can be attached to a limb. The insertion element can be an integrated part of the device or can be mechanically connected to the device.

The insertion element can repeatedly be attached to and removed from the retainer.

In one configuration of the insertion element, it can be interlocked with the retainer in order to mechanically secure the device to the limb. A force with at least a component perpendicular to the slide-in direction may be used for the interlocking process. The force can be an elastic force due to the elastic behaviour of the material of the insertion element, wherein the Young's modulus of the insertion element is between 0.5 GPa and 7 GPa in case the insertion element is made of a polymer.

In case the insertion element is made of a metal or a composite, Young's modulus of the insertion element may be between 50 GPa and 500 GPa.

Another embodiment of the device is characterized in that the limb connection system comprises a part of a ratchet system, having form elements in the shape of teeth with a latching function, wherein the form elements are capable of establishing a positive locking with a designated counterpart of the ratchet system. This mechanically connects and secures the device to the limb.

In one embodiment, such teeth may have a rounded shape.

The form elements can be one or more rows of teeth and counterpart can be one or more rows of teeth or recesses which are complementary in form and size. The counterpart can be part of an accessory or cuff, which is already or can be attached to the limb.

In one embodiment the limb connection system can function in a manner similar to a ratchet, with teeth that allow for incremental movement in at least one direction and thus adjustability of the fixture point of the device.

The ratchet system can allow the device to be repeatedly attached and removed from the counterpart at the limb.

The part of a ratchet system can be provided by teeth on the insertion element.

For the mechanical holding mount a swivel-mounted design may be provided, comprising a threaded connection between the mechanical holding mount and the limb connection system, wherein a bolt of the threaded connection passes through an opening in the mechanical holding mount, that is larger than the diameter of the bolt, thereby fixing the mechanical holding mount in a position along the direction of the bolt's longitudinal extension relative to the limb connection system. Thereby at least one guidance unit is provided for guiding the mechanical holding mount along an arcuate path in such a way that a pivoting movement of the mechanical holding mount in at least one rotational degree of freedom is enabled.

In this embodiment, the opening in the mechanical holding mount is essentially large enough to allow for play of the bolt in at least one direction perpendicular to the longitudinal axis of the bolt. As a result, the mechanical holding mount can pivot within the rotational degrees of freedom that the play, in combination with the guidance unit, allows.

For realising the threaded connection, a screw and a nut can be used. The nut can be located on the side of the mechanical holding mount or on the side of the limb connection system. The screw and the nut can control the friction in the swivel-mounted design. Loosening the screw can lead to enabling all movements and tightening the screw can lead to locking all movements. Once the desired orientation is reached, the user can tighten the screw to fix the relative angle of the mechanical holding mount.

The guidance unit can comprise a first arc-defining contact element on the radially inner side of the mechanical holding mount and a second arc-defining contact element on the radially outer side of the mechanical holding mount. The shape of the mechanical holding mount can locally match the arc-defining contact elements in form and size at its radially inner and outer sides, respectively. The mechanical holding mount may comprise an expulsion, which is designed to match the arc-defining contact elements in form and size.

Moreover, the first arc-defining contact element can be an arc-defining element which is either attached to the bolt or is an integral part of the bolt.

The second arc-defining contact element can be an integral part of the limb connection system.

Alternatively, the mechanical holding mount can be threadedly connected to a component which is only connected to the limb connection system, wherein the position of the mechanical holding mount is only indirectly fixed to the limb connection system. Consequently, said component can serve as the second arc-defining contact element.

The pivoting movement can be enabled in different rotational degrees of freedom until a certain limit. In one embodiment, the pivoting movement of the mechanical holding mount can have varying limits across different rotational degrees of freedom. As the pivoting movement in a certain rotational degree of freedom is guided through the guidance unit, the mechanical holding mount does not necessarily have to be able to pivot around a fixed point or axis. The movement can also be a combination of rotational and translational movement.

Due to the swivel-mounted design of the mechanical holding mount the device can be adjusted to establish a connection to different kinds of objects like for example handles from various angles. Additionally, a leverage can be adjusted by altering the angle of the mechanical holding mount.

For instance, the swivel mounted design can increase the compatibility for different shaped crutches. It can further improve the user experience, enabling the selection of the angle of the device relative to the handle of the crutch in a manner that minimizes additional leverage, thereby reducing discomfort.

In another embodiment, the opening in the mechanical holding mount has a conical form, and the guidance unit comprises a spherical segment-shaped calotte for guiding the mechanical holding mount along an arcuate path. This enables a pivoting movement of the mechanical holding mount in every rotational degree of freedom.

In this embodiment, the minimum radius of the calotte should be according to the following condition:

$$R=\cos(\alpha/2)\cdot x-r;$$

wherein r is the radius of the bolt, a is the opening angle of the conical opening, x is the diameter of the conical opening on its smaller side, and R is the minimum radius of the calotte. In case of a non-rotationally-symmetric hole, for instance when the hole has the shape of a slit, x is the maximum width of the slit, measured perpendicular to the length of the slit; and $\alpha$ is the opening angle in the plane where one would measure the width. The effect of this condition is that the calotte covers at least two opposing sides of the conical opening at any time, even if the mechanical holding mount is tilted to the full extent in any direction.

The smallest diameter of the conical opening is provided on a side of the mechanical holding mount where the calotte is positioned. The calotte does not necessarily need to be flat on the opposite side of its curved surface.

The opening in the mechanical holding mount can be a hole or bore with a conical shape, large enough to allow for play of the bolt in all directions perpendicular to the longitudinal axis of the bolt. As a result, the mechanical holding mount can pivot within all the rotational degrees of freedom that the play, in combination with the guidance unit, allows.

In a special embodiment, the opening can have any complex shape. For example, two slits can intersect, like a plus sign.

The guidance unit can comprise the spherical segment-shaped calotte as a first arc-defining contact element in contact with the radially inner side of the mechanical holding mount and an element with spherical segment-contoured cavity as a second arc-defining contact element in contact with the radially outer side of the mechanical holding mount. The shape of the mechanical holding mount can locally match the spherical segment-shaped calotte in form and size at its radially inner side and match the element with spherical segment-contoured cavity in form and size at its radially outer side.

Moreover, the spherical segment-shaped calotte can be an element which is either attached to the bolt or is an integral part of the bolt.

The element with spherical segment-contoured cavity can be an integral part of the limb connection system or a part of a component connected to the limb connection system.

In this embodiment, the spherical segment-shaped calotte gives the swivel-mounted design of the mechanical holding mount similar properties as a ball joint.

The rotational degrees of freedom of the mechanical holding mount may comprise a rotary movement around the longitudinal axis of the bolt. The rotary movement can be a 360° movement.

The guidance unit, comprising a spherical segment-shaped calotte, enhances the adjustability of the angle of the mechanical holding mount and improves user comfort. Thus, the device's versatility in connecting to various kinds of objects is expanded.

At least one belt of the device can comprise a hook-and-loop fastener.

In an alternative embodiment, at least one belt may comprise a buckle in order to fix end parts of the belt to each other.

A hook-and-loop fastener comprises, at least partially, a hook-and-loop system. The hook-and-loop fastener may enable the repeatable attachment to and removal of at least sections of the belt from the mechanical holding mount and/or the limb connection system.

In one embodiment, the mechanical holding mount may comprise at least a first slit, bar or buckle through or around which a first end section of the hook-and-loop fastener is or can be looped, and then is or can be attached to itself in order to fix it. A second slit or buckle located on the other side of the mechanical holding mount or at the limb connection system is or can be used to loop through the second end section of the hook-and-loop fastener in order to attach it to itself and to fix it. By this approach, an object in the mechanical holding mount can be secured. The fastening of the hook-and-loop-fastener can be executed under tensile tension.

Alternatively, the second slit or buckle can also be located at a component, which is only connected to the limb connection system, establishing an indirect connection to the limb connection system.

In one embodiment the device comprises a magnetic system having at least a first magnetic element located at one end section of the belt as well as at least one second magnetic element located at the limb connection system or at the mechanical holding mount. The magnetic system is configured in such a way that it facilitates the indirect fixation and/or positioning of said end section of the belt to the device when bringing the magnetic elements into magnetic coupling.

Mounting elements may be provided, having additional form elements in which the magnetic elements are integrated.

Aforementioned end section of the belt can be an end side area of the belt running in a loop, typically the area where the belt is folded over.

The first magnetic element located at the end section of the belt is essentially mechanically connected to the belt, for instance by means of the mounting element. The connection between the belt and the first magnetic element can be achieved by a slit, bar or buckle of the first mounting element, where the belt is looped around. In the case of the belt being a hook-and-loop fastener, it can then be attached to itself.

The second magnetic element can be in direct or indirect mechanical connection to the limb connection system.

By means of coupling the magnetic elements, the position of the corresponding end section of the belt can be fixed.

The magnetic system allows for faster and more convenient opening and closing of the belt. When the magnetic elements are brought into a position where they align, the attractive force between them is activated and the magnetic elements are pulled towards each other. The magnetic coupling can be released through the application of manual force. By means of the magnetic system, pre-tensioning of the belt can be achieved.

The device may comprise at least a first mounting element connected to the end section of the belt, having an undercut with a hook element open to a direction of at least a component of a tensile load transferred from the belt into the first mounting element. It may further comprise a second mounting element located at the limb connection system or at the mechanical holding mount, that is complementary in form and size to the undercut, so that the first mounting element is or can be fixed along the direction of the tensile load by means of the undercut, enabling the transmission of tensile load from the belt to the device.

The second mounting element can also be located at a component, which is connected to or a part of the limb connection system, establishing an indirect or direct connection to the limb connection system.

The aforementioned hook element of the undercut is an element that is capable of reaching behind a counter-element, which is part of the second mounting element. The hook element may also engage with said counter-element.

The first mounting element can be the same mounting element in which the first magnetic element is integrated and the second mounting element can be the same mounting element in which the second magnetic element is integrated.

In the case of two fixed end sections of the belt, the object in the mechanical holding mount can be secured and a force-fitting connection can be established to the object by means of the belt and the mounting elements. The described connection ensures a convenient opening and closing of the belt.

A further aspect of the present invention is an orthotic system, comprising a described device and a cuff mechanically connectable or connected to the device by means of the limb connection system.

An orthotic system, comprising the device and a cuff can be a convenient system for establishing a connection to a limb. When the cuff, for example, is connected to the forearm of an impaired person without hands, the person can connect the device to the cuff and consequently benefits from all the functions of the device, enabling performing tasks that typically require the use of hands.

As a result, the person can, for instance, use crutches by connecting the device to the handles of the crutch via the mechanical holding mount. The cuff can serve as a pleasant limb accessory for creating a reversible connection to the forearm and allows to connect modules like the device.

One embodiment of the cuff comprises a cuff base in form of a lower shell and a fixation element which can be combined or is combined with the lower shell into a sleeve attachable to a limb through direct or indirect interlocking with each other, wherein the lower shell and the fixation element provide a system that can be tightened around the limb by reducing a circumference formed by the lower shell and the fixation element, such that load transfer from an accessory to the limb is enabled.

The insertion of a limb, for instance a forearm, into the cuff can be difficult as, in most cases, there is an enlargement at the beginning of the palm. In order to facilitate the insertion of the cuff, in this embodiment the cuff design is divided into a cuff base in form of a lower shell and a fixation element, which can be a cuff top in form of an upper shell, or a strap system.

The possible reduction of the circumference formed by the lower shell and the fixation element, for example, with a strap system or a lacing system can provide a fast and comfortable way to interlock the cuff with the forearm.

Such a system can ensure that a load can be transferred from the cuff to the forearm or from the forearm to the cuff. When the cuff is further connected to the device, the load can be also transferred to or from the device.

In one embodiment of the orthotic system according to the invention, the cuff base comprises a first part of a ratchet system and the device comprises a second part of the ratchet system, wherein the first part and the second part have form elements with a latching function, respectively, which are complementary in form and size in order to establish a positive locking.

By interlocking the first part of the ratchet system with the second part of the ratchet system the cuff is mechanically connected to the device. The cuff is or can be connected to the limb, which means an indirect mechanical connection of the device to the limb is or can be established.

One of the elements of cuff and device may comprise a retainer equipped with either the first part or second part of the ratchet system and the respective other element of cuff and device may comprise an insertion element that is intended to be positioned in the retainer. The insertion element is equipped with the respective other first part or second part of the ratchet system and is designed to be pushed into the retainer along a slide-in direction, and due to an application of force, to bring the first part and second part in a positive locking.

When bringing the insertion element and the retainer into positive locking, at least a component of the force needed is perpendicular to the slide-in direction.

In one embodiment, the cuff can comprise the retainer with the first part of the ratchet system and the limb connection system of the device can comprise the insertion element with the second part of the ratchet system.

The application of force may be realized by an elastic behaviour of the insertion element pushing the respective first part or second part of the ratchet system in the direction of the respective first part or second part at the retainer in order to establish the positive locking, wherein the Young's modulus of the insertion element is between 0.5 GPa and 7 GPa.

The insertion element may be bent while inserting the insertion element into the retainer. Thereby the retainer is configured to absorb the induced bending moment, enabling the application of force needed to establish a positive locking.

The elasticity of the insertion element can be adapted in such a way that the insertion element can be manually elastically bent and thus partially be moved by applying a pressing force of at least 3 N, thereby disengaging the first part and second part of the ratchet system from the positive locking. This allows the user to manually remove the positive locking if desired.

At least a component of the pressing force is essentially perpendicular to the slide-in direction.

The device can comprise a button designated for applying the pressing force, wherein the button may be provided in the end section of the insertion element which is adapted to be pushed into the retainer.

A plurality of first parts and second parts of the ratchet system may be arranged in rows, respectively, so that the positive locking can be realized at different positions along the slide-in direction.

In one embodiment the first parts and second parts of the ratchet system can be a row of teeth or recesses, respectively. The arrangement in rows can allow for incremental movement in at least one direction and thus adjustability of the fixture point of the device at the cuff. The adjustment of the fixture point can, for example, be executed by disengaging, repositioning, and relocking the ratchet system.

The insertion element may comprise a bridging section, comprising teeth forming a serration, and support elements located ahead and behind the bridging section in relation to the slide-in direction for supporting the insertion element on support parts provided by the retainer, with the support elements protruding at an angle from the bridging section with respect to the slide-in direction, respectively, wherein the teeth of the insertion element and the teeth of the retainer are configured such that they can be interlocked in an engaged state in a plane of engagement, wherein the retainer forms an enclosure for the insertion element, blocking at least one rotational degree of freedom of the inserted insertion element around an axis perpendicular to the slide-in direction, wherein the bridging section and/or the support element located at the end of the bridging section are provided by a material having a Young's modulus between 0.5 GPa and 7 GPa, so that when a manual force is applied to the bridging section, the bridging section and/or said support element is able to elastically deform, resulting in the disengagement of the teeth of the insertion element and the teeth of the retainer.

The protruding angle of at least one support element can be in a range of 20° to 160° to the plane of engagement.

Furthermore, the support elements can be arranged in such a way, that the insertion element has a portal-shaped form.

The axis of the restricted rotational degree of freedom of the insertion element is parallel to the plane of engagement of the teeth of the insertion element and the teeth of the retainer, and perpendicular to the slide-in direction.

The mechanical holding mount of the device can be made from a flexible material with a Young's modulus between 0.5 GPa and 7 GPa, thereby allowing it to adapt its form to the geometry of the object positioned in the mechanical holding mount.

However, in case the mechanical holding mount is made of a metal or a composite, Young's modulus of the mechanical holding mount may be between 50 GPa and 500 GPa.

An elastic material of the mechanical holding mount, in combination with its design, can contribute to a force-fitting connection to the object positioned in the mechanical holding mount.

The connection between the device and the cuff that is described above and in the following in connection with the figures is only a preferred embodiment of the invention. In other embodiments it also possible that the device is integrally formed with the cuff (or any other structure that is directly connectable to the limb of a person).

BRIEF DESCRIPTIONS OF THE DRAWINGS

The invention is illustrated by the following examples and figures, from which further embodiments and advantages can be drawn. These examples are meant to illustrate the invention but not to limit its scope.

It is shown in

Figure 2:
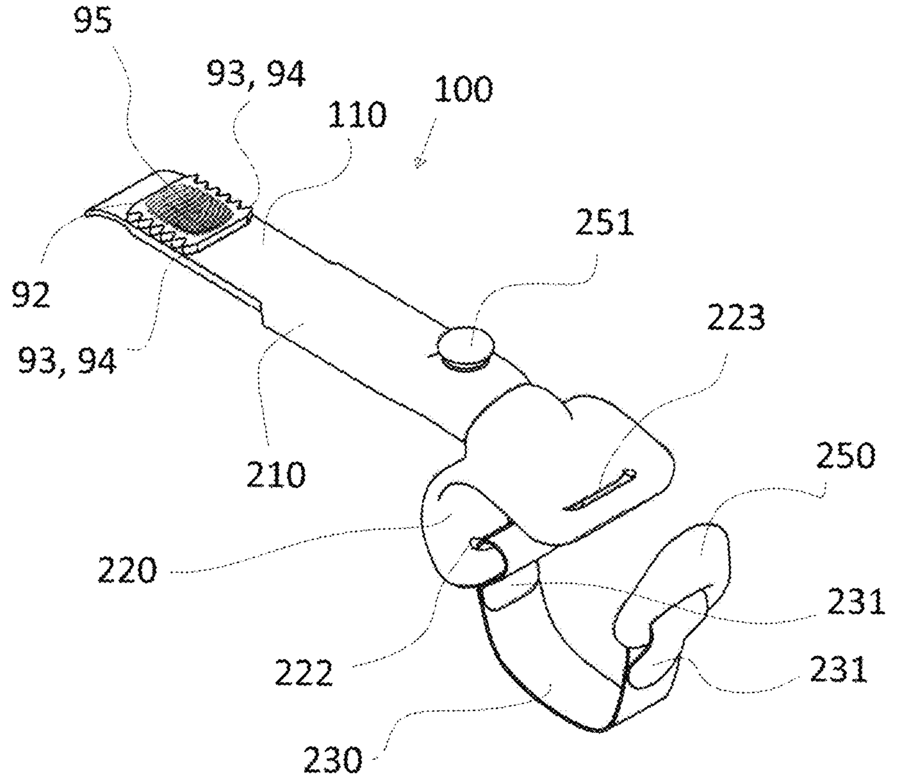
Figure 3:
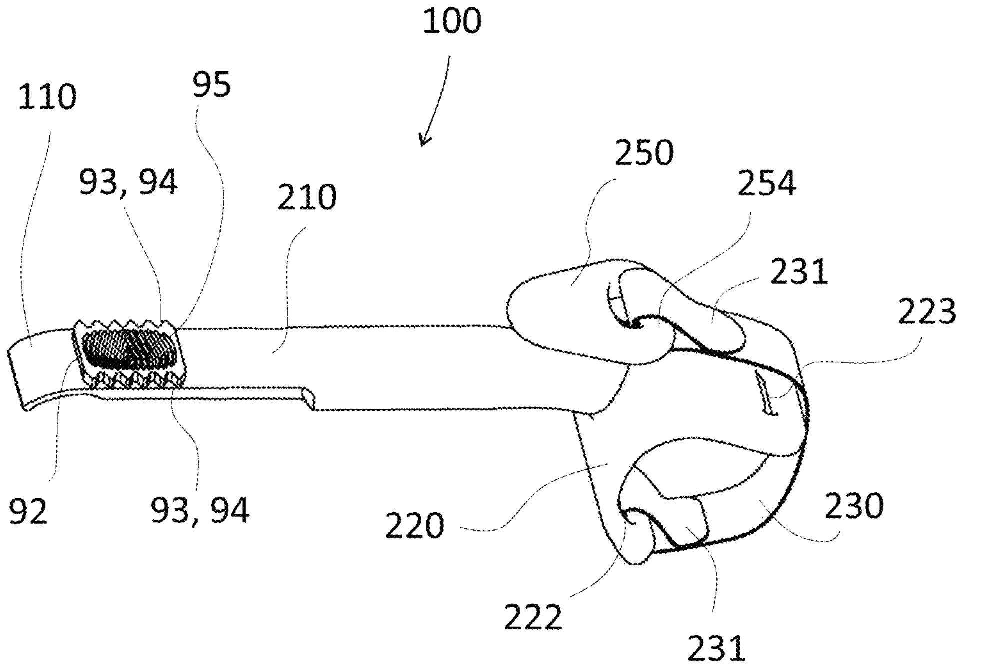
Figure 4:
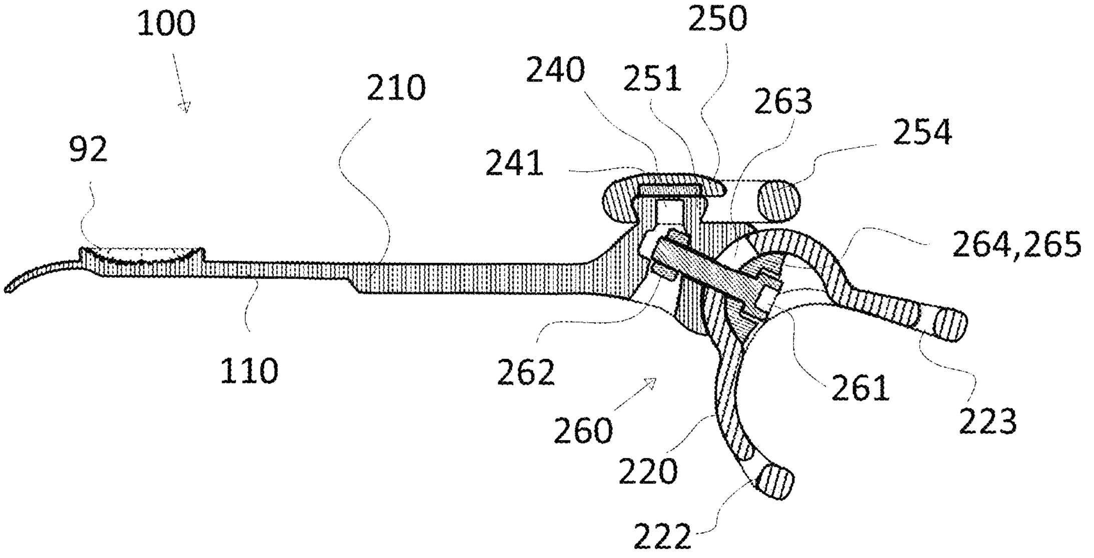
Figure 5:
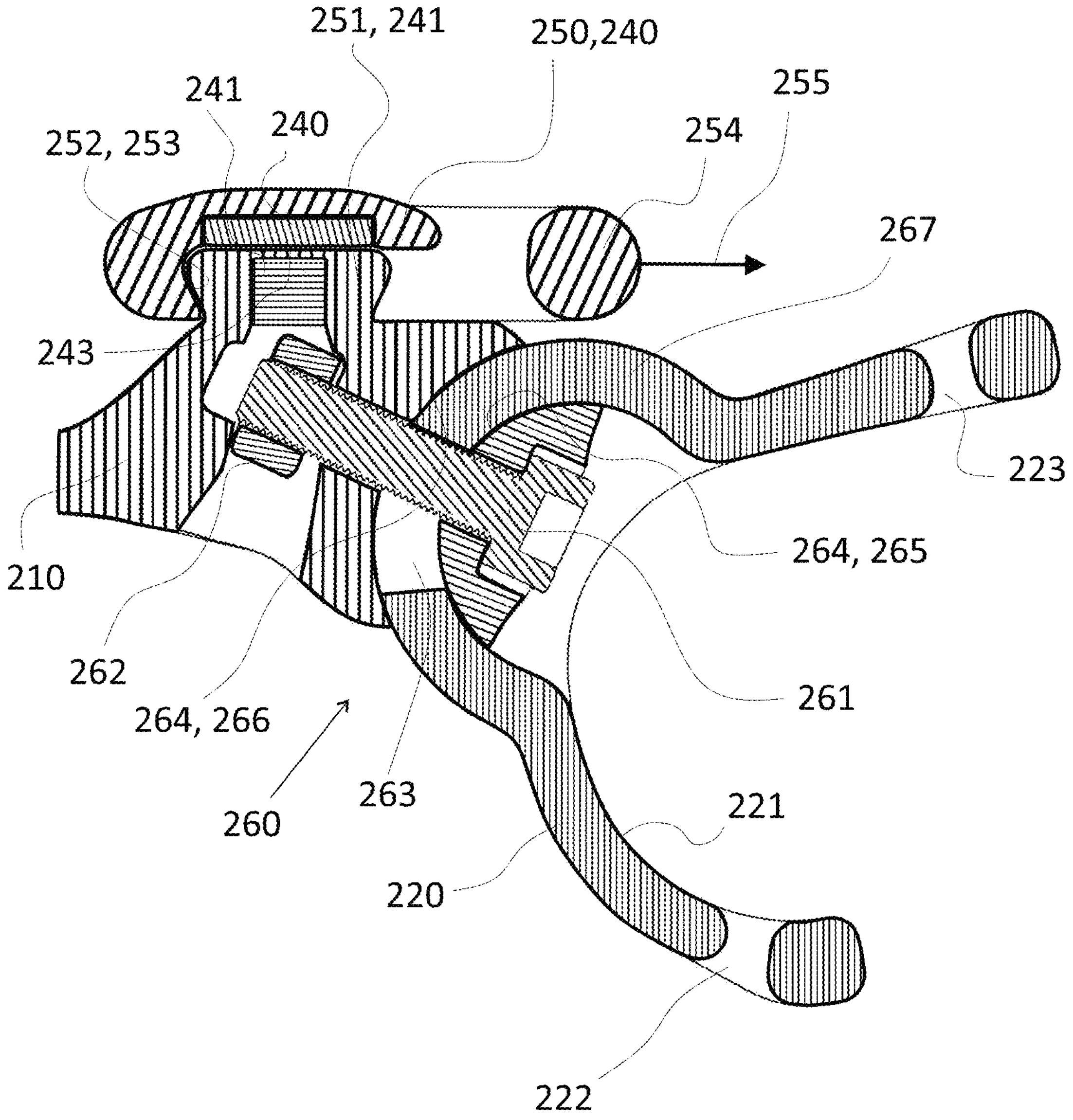
Figure 6:
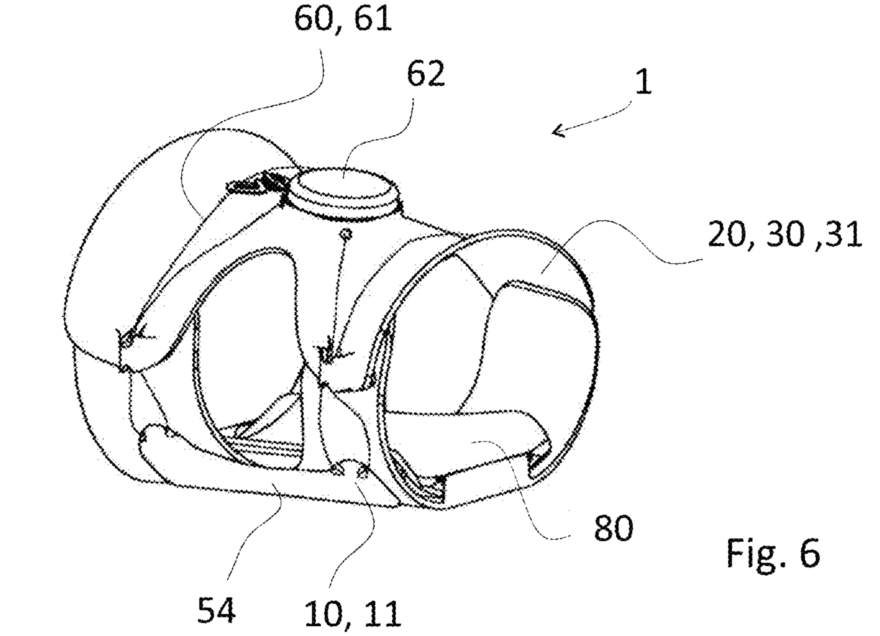
Figure 7:
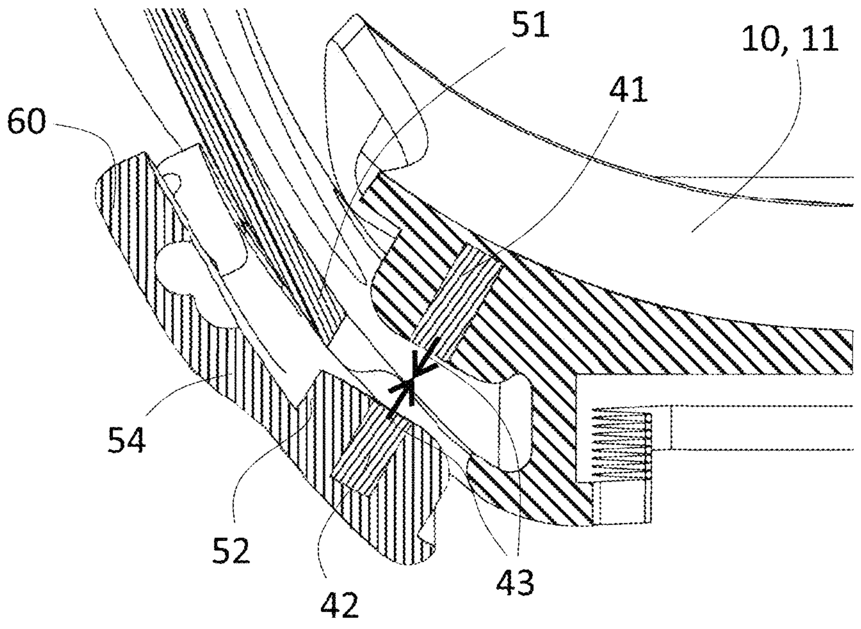
Figure 8:
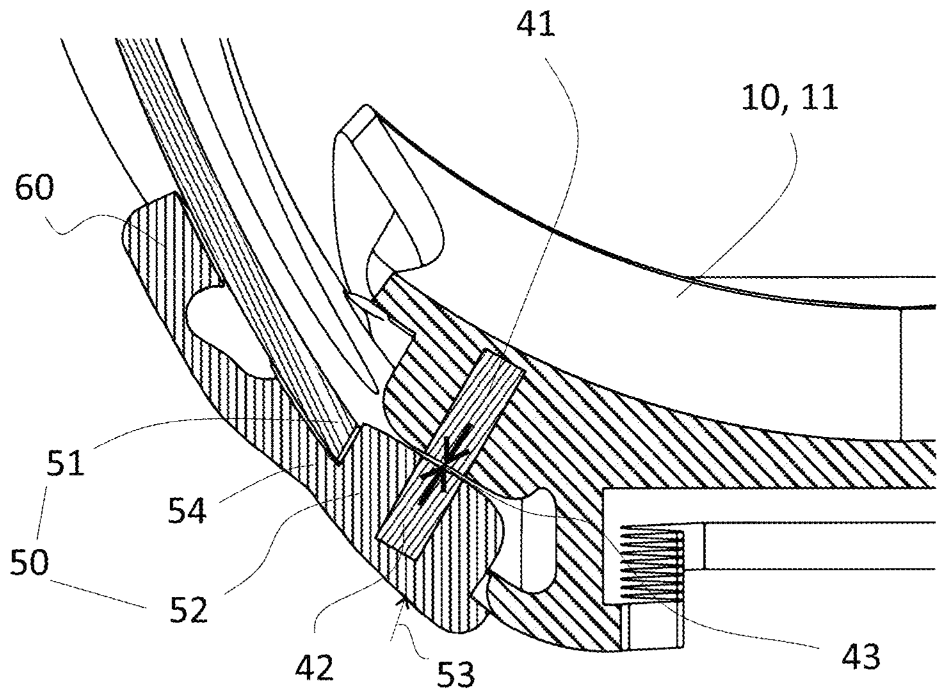
Figure 9:
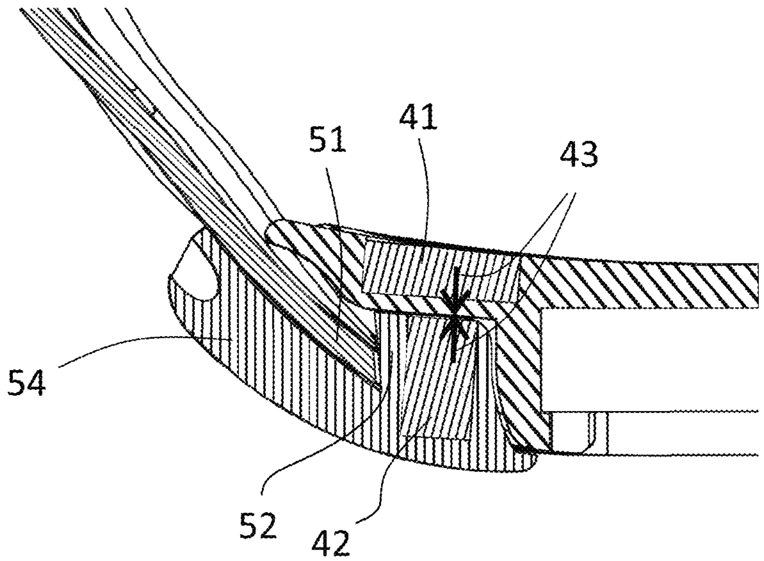
Figure 10:
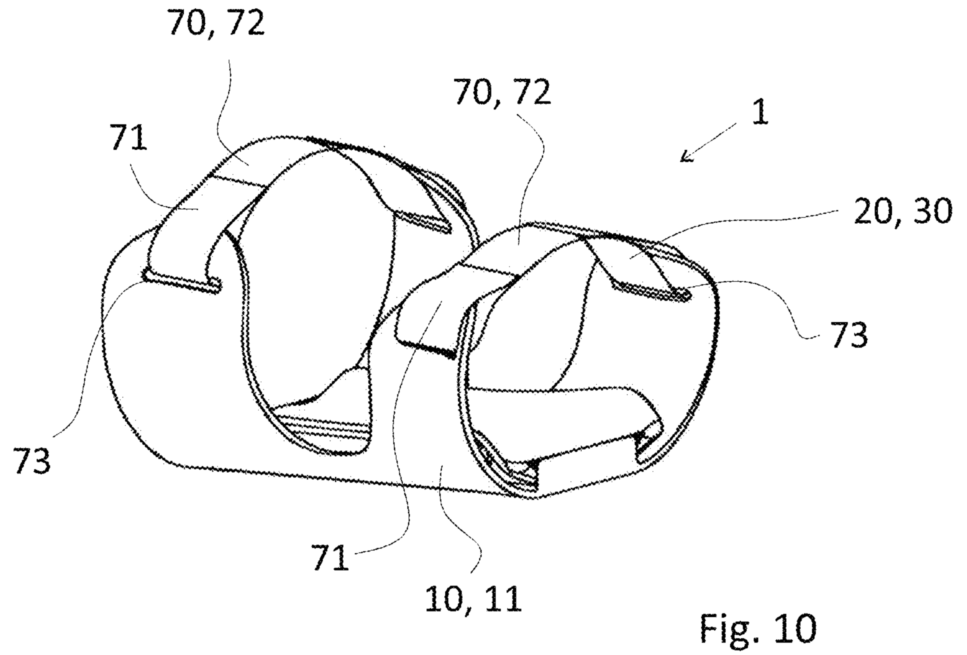
Figure 11:
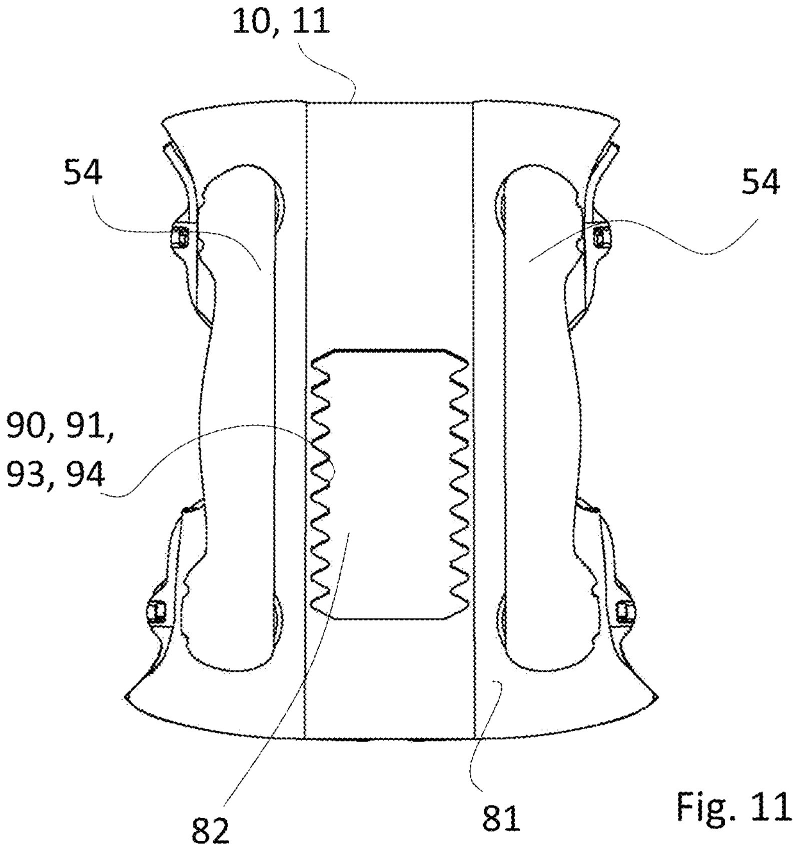
Figure 12:
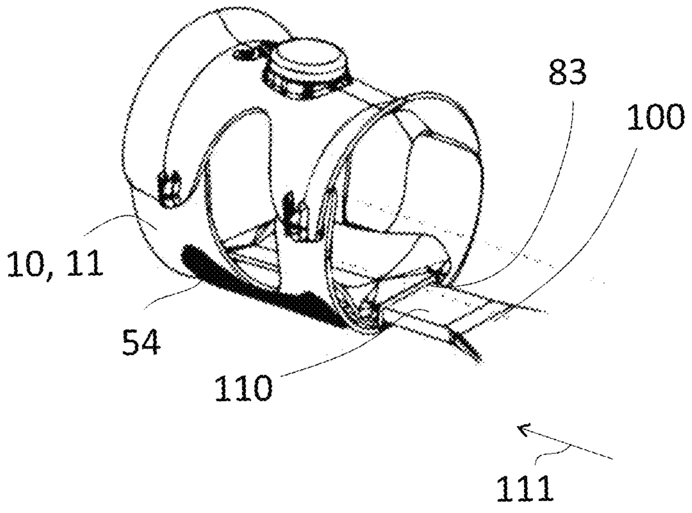
Figure 13:
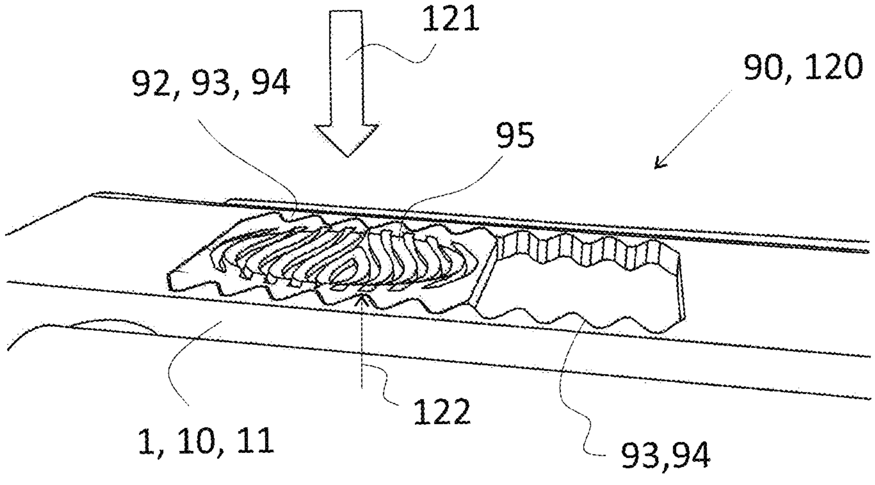
Figure 14:
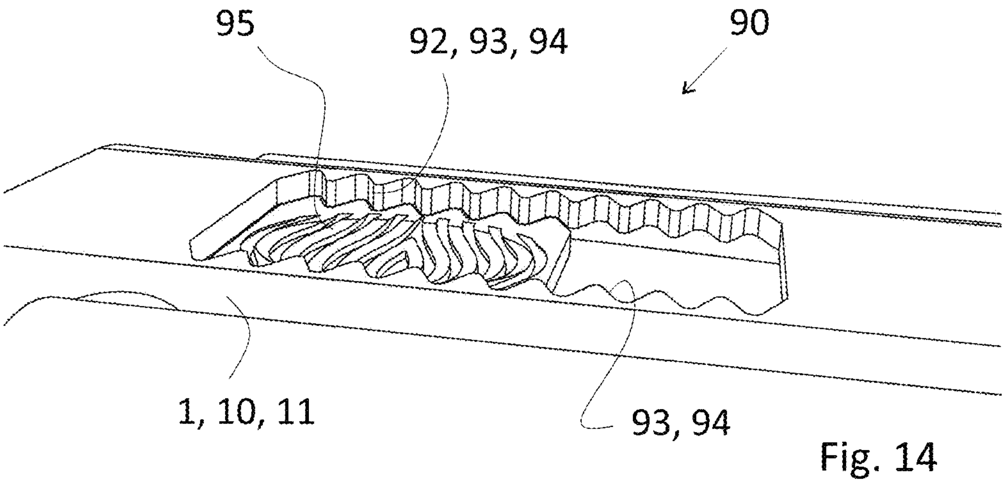
Figure 15:
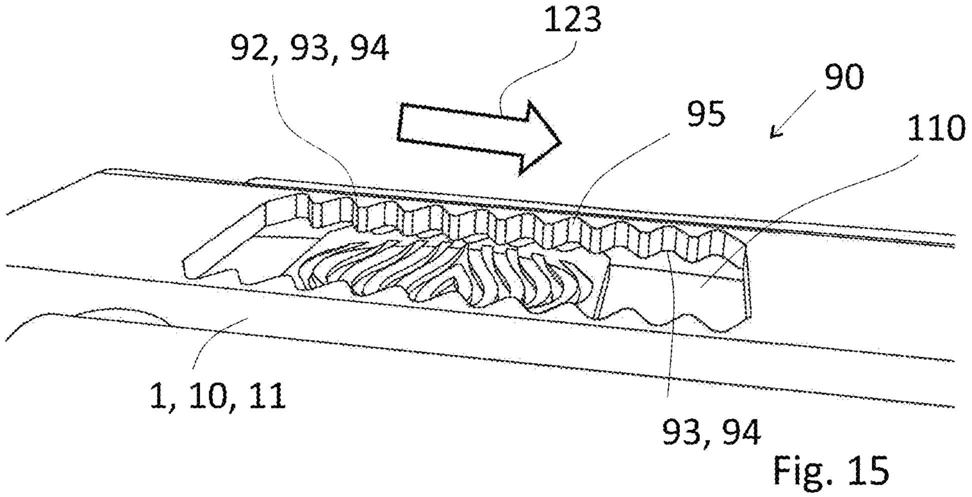
Figure 16:
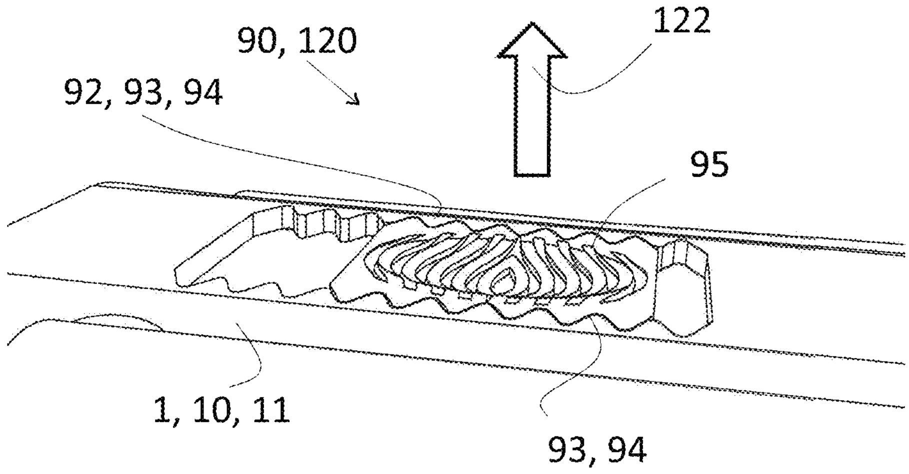

FIG. 1: a first embodiment of the device in a perspective view,

FIG. 2: a second embodiment of the device in a perspective view in a first state, FIG. 3: perspective view of the device shown in FIG. 2 in a second state, FIG. 4: a cross sectional view of the device shown in FIG. 2 and FIG. 3 in the second state, FIG. 5: a detailed partial cross sectional view of FIG. 4 with the device in a third state, FIG. 6: a first embodiment of the cuff in a perspective view, FIG. 7: a partial sectional view of the cuff shown in FIG. 6 before form fit connection, FIG. 8: the partial sectional view of the cuff shown in FIG. 6 in form fit connection, FIG. 9: a further embodiment of the cuff shown in FIG. 6 in form fit connection, FIG. 10: a second embodiment of the cuff in a perspective view, FIG. 11: the underside of the cuff shown in FIG. 6, FIG. 12: an orthotic system with a module other than the device in a perspective view, FIG. 13: a part of the cuff as well as a part of the device in a first state, FIG. 14: the part of the cuff as well as the part of the device in a second state, FIG. 15: the part of the cuff as well as the part of the device in a third state, and FIG. 16: the part of the cuff as well as the part of the device in a fourth state.

DETAILED DESCRIPTION

FIG. 1 shows a device 100 in a perspective view in accordance to the invention. The device 100 comprises a limb connection system 210 which has an elongated shape. Part of the limb connection system 210 is an insertion element 110 that is equipped with a second part of a ratchet system 92 comprising form elements 93 in the shape of teeth 94 and a button 95.

There are two rows of teeth 94 that are located on top of the insertion element 110. The row of teeth 94 are facing into opposite directions, pointing sideways away from the insertion element 110 and away from the button 95. The location of such form elements 93 may differ.

The button 95 is designed to be manually pushed against the elastic force of the slightly curved insertion element 110. A first part of the ratchet system 91 is shown in FIGS. 13 to 16 as part of a connected cuff 1. The second part of the ratchet system 92 can be disengaged from a positive locking 120 in a convenient way by pressing the button 95.

The device 100 further shows a mechanical holding mount 220, which has a cavity 221 to establish a form fitting connect with an object. A belt 230 with an integrated hook-and-loop fastener 231 is connected at two sides of the cavity 22. The form of the belt 230 illustrates how an object can be wrapped in order to fix its position. Thereby the belt 230 eventually applies tensional force to establish a force-fitting connection to the object.

As shown in FIG. 2, another embodiment of the device 100 comprises an identical limb connection system 210, but a different mechanical holding mount 220. Moreover, a different connection system of the belt 230 is demonstrated. Both end sections of the belt 230 comprise a hook-and-loop fastener 231, respectively. The belt 230 is shown is opened state.

One end section of the belt 230 is threaded through a first slit 222 at the mechanical holding mount 220 and attached to itself, while the other end section is attached in a similar way to a first mounting element 250. The second mounting element 251 is located at the limb connection system 210. In order to close the belt 230, the first and the second mounting elements 250, 251 can be brought into a form-fitting connection.

Additionally, the mechanical holding mount comprises a second slit 223, where the belt 230 optionally can be connected or which can be used as guidance for the belt 230.

FIG. 3 shows the device 100 in the same embodiment as shown in FIG. 2, wherein the belt 230 is in a closed state. The first and the second mounting elements 250, 251 are depicted in a connected state. Thereby, the first mounting element 250 blocks the view onto the second mounting element 251. The first mounting element 250 further comprises a bar 254, where the belt 230 is looped around and connected to itself by means of the hook-and-loop fastener 231. The opposite end section of the belt 230 is also equipped with a hook-and-loop fastener 231, which is connected to the first slit 222 of the mechanical holding mount 220 in a similar manner. The slit 223 either can be used for guidance purposes of the belt 230 or can be used to fixture one end section of the belt 230.

FIG. 4 depicts a cross sectional view of the device 100 according to FIG. 2, and FIG. 3 in the same state as FIG. 3. In this illustration, the belt is concealed, revealing a clearer view of the two slits 222, 223. As can be seen here, the mounting elements 250, 251 are in a connected state.

The first mounting element 250 comprises a first magnetic element 240 while the second mounting element 251 comprises a second magnetic element 241. By means of magnetic attraction between the first magnetic element 240 and the second magnetic element 241, the first and second mounting elements 250,251 are brought into a form-fitting connection. In this case, the second mounting element is a part of the limb connection system 210. As the belt 230 can be connected to the first mounting element 250, the magnetic elements 240, 241 enable a guided opening and closing of the belt 230 in a user-friendly way.

In addition, the sectional view reveals the swivel mounted design 260 of the mechanical holding mount 220. The mechanical holding mount is connected to the limb connection system 210 by means of a bolt 261 and a nut 262. The bolt 261 first passes through a first arc-defining contact element 265 as part of a guidance unit 264, then through an opening 263 in the mechanical holding mount 220, and finally through an opening in the limb connection system 210 before being tightened with the nut 262. The said opening 263 in the mechanical holding mount 220 allows for play of the bolt, so that in the illustrated position a pivoting movement of the mechanical holding mount 220 can be executed counterclockwise.

FIG. 5 shows the swivel mounted design 260 of the mechanical holding mount 220 in a partial cross sectional view. The detailed view depicts a second state of the same embodiment as FIG. 4. In this state, the pivoting movement has reached its limit in counterclockwise direction only allowing for the reverse movement of the mechanical holding 220 in clockwise direction. In this position, the bolt 261 has a different position within the opening 263 of the mechanical holding mount 220.

The geometrical form of the limb connection system 210 at the opening where the bolt passes through is shaped to serve as a second arc-defining contact element 266. The first arc-defining contact element 265 and the second arc-defining contact element 266 together form the guidance unit 264 for enabling a guided pivoting movement of the mechanical holding mount 220. The mechanical holding mount 220 has an expulsion 267 with local contact surfaces that match the guidance unit 264 in form and size.

Moreover, FIG. 5 shows, that the first mounting element 250 comprises an undercut 252 with a hook element 253. The undercut 252 is in a state of form-fitting connection with the second mounting element 251. The magnetic elements 240, 241 are aligned and in a state of magnetic coupling 243. The combination of using the magnetic elements 240, 241 and the undercut 252 enables a fast and secure way to open and close the end section of the belt 230. The undercut 252 further enables the transfer of a tensile load 255 that is applied from the belt 230 to the first mounting element 250 and then by means of the undercut 252 to the limb connection system 210.

There can be various systems to establish a mechanical connection from the device 100 to a limb. One system can be a cuff 1 that is attachable to the limb in accordance to the invention. The cuff 1 further comprises a first part of the ratchet system 91, which is compatible to establish a mechanical connection to the second part of the ratchet system 92 of the device 100.

Insertion of a limb, for instance a forearm, into the cuff 1 can be difficult as, in most cases, there is an enlargement at the beginning of the palm. This makes it difficult to insert the arm into the cuff 1 from the proximal side. In order to facilitate the insertion of the arm into the cuff 1 on the proximal side, the design is divided into a cuff base 10 in form of a lower shell 11 and a fixation element 20, which can be a cuff top 30 in form of an upper shell 31, see FIG. 6, or a strap system 70, see FIG. 8.

As shown in the embodiment of FIG. 6, the shells 11, 31 can be separated as two distinct elements. The lower shell 11 can in this case be set radially to the axis of the arm. The upper shell 31 can then be coupled to the lower shell 11 to create a closed system around the forearm.

The number of shells 11, 31 can be larger than two and rise to three, four or more, but that can be the case only if they can be linked in such a way that the user does not need to hold them all in position before tightening them together around their forearm.

The way in which the shells can be connected to each other should be easy and effortless. In the embodiment shown in FIG. 6, the upper shell 31 as the fixation element 20 is connected to the lower shell by means of the lacing system 60, which comprises second form fit means 52, which is adapted to allow a geometrical interlocking with first form fit means 51 of the lower shell 11 on demand. Through this, the second form fit means 52 and the first form fit means create a form fit connection 50.

This means that the second form fit means 52 can be disconnected from the lower shell 11 whenever it is desired. The second form fit means 52 acts as a hook.

Each second form fit means 52 is provided at a lacing element 61 in form of a cable, which is connected with a lacing knob 62. By turning of the lacing knob, tension is generated in the lacing element, which causes the tightening of the lacing system 60.

As the tension generated in the lacing system 60 increases, the circumference becomes reduced, allowing the lacing system 60 to be tightened around the forearm which results in better transmission of the forces exerted on the cuff 1.

The fixation element 20 in form of the upper shell 31 comprising the lacing system 60 may comprise according to the embodiment shown in FIG. 6 a common part 54 at which a plurality of the second form fit means 52 are provided. Thus, at the lower shell a number of the first form fit means 51 is provided accordingly.

As shown in FIGS. 7 to 9, in order to increase the user friendliness, at least one first magnetic part 41 is positioned in the body of the lower shell 11, and at least one second magnetic part 42 is positioned in the second form fit means 52 at the lacing system. In the case of the use of a common part at which a plurality of the second form fit means 52 are provided, a corresponding number of second magnetic parts 42 is provided at this common part 54, too.

Thus, the second magnetic part 43 and therefore the hook of the second form fit means is guided by the attracting magnetic force 43 of both magnetic parts 41, 42 into the first form fit means 51 in the lower shell 11 along the insertion direction 53, shown in FIG. 7.

The magnetic parts 41, 42 then hold the form fit means 51, 52 in place by means of the attracting magnetic force 43, therefore creating a magnetic connection 40, see FIG. 8. Once tension is set in the lacing system 61, the magnetic parts 41, 42 no longer play a role, since the form fit means 51, 52 are geometrically interlocked, for instance by means of an undercut, shown in FIG. 7.

Once the form fit means 51, 52 are in place in the lower shell 11, the lacing system 60 can start to be operated. The higher the cable tension, the more difficult it becomes to remove the form fit means 51, 52. The cuff top 30 slides on the cuff base 10 when the lacing system 60 gets tightened.

The number of form fit means 51, 52 can vary, and the form fit means 51, 52 can be positioned at different positions, as shown in FIG. 9. The interlocking form fit means 51, 52 can also be integrated into the shells, in this case the shells must be deformed when the lacing system 60 is being operated.

In order to remove the cuff 1, the user must release the tension of the lacing system 60 and pull radially on the second form fit means 52, or on the lacing element 61. The cuff 1 can be removed, once the second form fit means 52 is released.

In FIG. 10, a different embodiment of the cuff 1 is shown. In this embodiment, the cuff 1 provides a cuff base 10 in form of a lower shell 11 and a fixation means 20 in form of a strap system 70. The strap system 70 comprises two straps 71 which are led through cutouts 73 of the cuff base 10. The straps 71 are provided with a hook-and-loop system 72, respectively.

By tensioning the straps 71 and fixation of the hook-and-loop system 72, the strap system 70 can be tightened around the forearm.

The embodiment of the cuff 1 comprising a strap system 70 is not restricted to the embodiment shown in FIG. 10.

A further embodiment not shown here may comprise a hook-based closure, similar or equal to the common part 54 at which a plurality of the second form fit means 52 and/or second magnetic parts 42 are provided and which is shown in FIG. 6.

When the user places the cuff base 10 on his arm, the second form fit means 52 approaches its position, thanks to the attracting magnetic force 43 of the magnetic parts 41, 42. The user can tighten the strap system 70 with one hand thereby achieving an adjusted tighter or looser fit of the cuff 1 on the arm.

In both embodiments shown in FIGS. 6 and 8, cushioning material 80 is applied in the cuff base 10.

Another aspect of the design is its modularity.

The system allows for the connection of different modules to best meet the needs of the users. Especially, it can be connected to the device 100. The device 100 can be inserted into the lower shell 11 of the cuff 1.

FIG. 12 depicts the insertion of the device 100 into the cuff 1, wherein the device 100 is only partly illustrated. As shown, the insertion element 110 of the device 100 can be directly inserted along a slide-in direction 111 into a retainer 82, which is provided in the cuff base 10 through an insertion slot 83 which in turn is arranged at the distal end of the cuff 1, shown in FIG. 11.

Once the insertion element 110 of the device 100 is inserted in the insertion slot 83, the user has to press the button 95, shown in FIGS. 13 to 16, and slide the insertion element 110 of the device 100 into the lower shell 11, while keeping the button 95 pressed. Here, the button 95 is a special design on the insertion element 110 of the device 100, which slides into the lower shell 11. The user can then release the button 95 when the desired position is reached.

For fixation of different positions of the device 100 with regard to the cuff 1, the orthotic system comprising the cuff 1 and device 100 further comprises a ratchet system 90. The ratchet system 90 comprises the first part 91 provided at the lower shell 11 of the cuff 1, as well as the second part 92 provided at the insertion element 110 of the device 100 and/or at the button 95. Both components 91, 92 of the ratchet system 90 feature form elements 93, having a shape like teeth 94. In an embodiment, these teeth 94 may have a rounded shape.

The form elements 93 of the first part 91 and the second part 92 are complementary to each other in form and size.

Positive locking 120 of these form elements 93 allows the transfer of loads along the slide-in direction 111, shown in FIG. 12.

Furthermore, the device 100 can slide along the slide-in direction 111 parallel to an arm axis. Depending on the activity and intensity, different positions of the device 100 along the slide-in direction 111 might be required. This allows for the same design to be used by users with different arm lengths.

The distance between the area of interest of the device 100 and the insertion slot 83 of the lower shell 11 as seen in FIG. 12 can be adjusted by means of the ratchet system 90.

The number of positions of the device 100 is determined by the number of form elements 93 on the first part 91 and the second part 92 of the ratchet system 90.

FIGS. 13 to 16 show a method for changing the position of the device 100 with respect to the cuff.

In FIGS. 13 to 16 a part of the lower shell 11 or the cuff base 10 of the cuff 1 is shown, as well as a part of the insertion element 110 of a device 100, which is not shown completely.

At the insertion element 110 the button 95 is provided.

In the retainer 82 of the lower shell 11 the first part 91 of the ratchet system 90 is provided, comprising a plurality of form elements 93 in the shape of teeth 94, respectively.

At the insertion element 110 and/or at the button 95 the second part 92 of the ratchet system 90 is provided, comprising also a plurality of form elements 93 in the shape of a teeth 94, respectively.

The form elements 93 of the first part 91 and of the second part 92 of the ratchet system 90 are arranged in rows, respectively, and are complementary to each other in form and size.

FIG. 13 shows a state in which the form elements 93 of the first part 91 and the second part 92 engage with each other. Thus, a positive locking 120 is established between the lower shell 11 and the insertion element 110. This engaged state is maintained by means of a force 122 acting on the insertion element 110 due to elasticity of the insertion element 110.

When the button 95 is pressed by a pressing force 121, for instance manually, the button 95 and therefore the insertion element 110 is pressed inward against the elastic force 122, wherein the form elements 93 of the first part 91 and of the second part 92 of the ratchet system 90 are moved out of their engagement, so that the positive locking 120 does not exist anymore, as shown in FIG. 14.

When the insertion element 110 has been moved inward, by applying a moving force 123 on the button 95, the insertion element 110 can be moved parallel to the extension of the rows of form elements 93 of the first part 91 and of the second part 92 of the ratchet system 90. Thus, the position of the insertion element 110 and therefore the position of the device 100 with respect to the cuff 1 can be adjusted, see FIG. 15.

When the foreseen position has been reached, the button 95 can be released and due to elastic force 122 the insertion element 110 as well as the button 95 moves so that the form elements 93 of the first part 91 and of the second part 92 of the ratchet system 90 engage again, shown in FIG. 16.

The device 100 can be removed from the cuff 1, when necessary, for example, if the targeted activity changes, requiring another module.

The orthotic system allows for outdoor activities and can be used for muscle-strengthening sessions or fitness training It can also be used in the water, for example, when kayaking. These activities require a critical degree of freedom so as not to restrict the movement of the upper limbs. The system then allows for symmetrical body development through the activities being practised. Furthermore, it can be used of person with manual impairment to walk on crutches without using their hands.

LIST OF REFERENCE SIGNS

1 cuff
10 cuff base
11 lower shell
20 fixation element
30 cuff top
31 upper shell
40 magnetic connection
41 first magnetic part
42 second magnetic part
43 attracting magnetic force
50 form fit connection
51 first form fit means
52 second form fit means
53 insertion direction
54 common part
60 lacing system
61 lacing element
62 lacing knob
70 strap system
71 strap
72 hook-and-loop system
73 cutout
80 cushioning material
81 distal end
82 retainer
83 insertion slot
90 ratchet system
91 first part of the ratchet system
92 second part of the ratchet system
93 form element
94 teeth
95 button
100 device
110 insertion element
111 slide-in direction
120 positive locking
121 pressing force
122 force
123 moving force
210 limb connection system
220 mechanical holding mount
221 cavity
222 first slit
223 second slit
230 belt
231 hook-and-loop fastener
240 first magnetic element
241 second magnetic element
243 magnetic coupling
250 first mounting element
251 second mounting element
252 undercut
253 hook element
254 bar
255 tensile load
260 swivel-mounted design
261 bolt
262 nut
263 opening
264 guidance unit
265 first arc-defining contact element
266 second arc-defining contact element
267 expulsion

The invention claimed is:

1. A device for establishing a form-fitting and/or force-fitting connection to an object, comprising at least one limb connection system designed to achieve a mechanical attachment to a limb of a person, as well as a mechanical holding mount in which the object can be positioned, such that load transfer from the object to the limb is enabled, and at least one belt mechanically connected to said holding mount, wherein the belt is configured to be partially wrapped around the object positioned in the mechanical holding mount in order to fix the object in at least one translational degree of freedom, wherein the device comprises at least a first mounting element connected to the end section of the belt, having an undercut with a hook element open to a direction of at least a component of a tensile load transferred from the belt into the first mounting element, and further comprising a second mounting element located at the limb connection system and/or at the mechanical holding mount, that is complementary in form and size to the undercut, so that the first mounting element is or can be fixed along the direction of the tensile load by means of the undercut, enabling the transmission of tensile load from the belt to the device;

wherein the device comprises a magnetic system having at least a first magnetic element located at one end section of the belt as well as at least one second magnetic element located at the limb connection system or at the mechanical holding mount, in such a way that the magnetic system facilitates the indirect fixation and/or positioning of said end section of the belt to the device when bringing the magnetic elements into magnetic coupling.

2. The device according to claim 1, characterized in that the limb connection system comprises an insertion element, which is designed to be pushed along a slide-in direction into a retainer attached to a limb, wherein the insertion element has a transversal extension and a longitudinal extension longer than the transversal extension and can be inserted along its longitudinal extension into the retainer such that at least one translational degree of freedom perpendicular to the slide-in direction of the insertion element is blocked or can be blocked by the retainer.

3. The device according to claim 1, wherein the limb connection system comprises a part of a positive locking system, having form elements in the shape of teeth with a latching function, wherein the form elements are capable of establishing a positive locking with a designated counterpart of the positive locking system, which mechanically connects and secures the device to the limb.

4. The device according to claim 1, wherein the mechanical holding mount has a swivel-mounted design, comprising a threaded connection between the mechanical holding mount and the limb connection system, wherein a bolt of the threaded connection passes through an opening in the mechanical holding mount, that is larger than the diameter of the bolt, thereby fixing the mechanical holding mount in a position along the direction of the bolt's longitudinal extension relative to the limb connection system, and wherein at least one guidance unit is provided for guiding the mechanical holding mount along an arcuate path in such a way that a pivoting movement of the mechanical holding mount in at least one rotational degree of freedom is enabled.

5. The device according to claim 4, wherein the opening in the mechanical holding mount is a conical opening, and the guidance unit comprises a spherical segment-shaped calotte for guiding the mechanical holding mount along an arcuate path in such a way that a pivoting movement of the mechanical holding mount in every rotational degree of freedom is enabled.

6. The device according to claim 1, wherein the at least one belt comprises a hook-and-loop fastener.

7. An orthotic system, comprising the device according to claim 1 and a cuff mechanically connectable or connected to the device by means of the limb connection system.

8. The orthotic system according to claim 7, wherein the cuff comprises a cuff base in form of a lower shell and a fixation element which can be combined or is combined with the lower shell into a sleeve attachable to a limb through direct or indirect interlocking with each other, wherein the lower shell and the fixation element provide a system that can be tightened around the limb by reducing a circumference formed by the lower shell and the fixation element, such that load transfer from an accessory to the limb is enabled.

9. The orthotic system according to claim 8, wherein the cuff comprises a first part of a positive locking system and the device comprises a second part of the positive locking system and wherein the first part and the second part have form elements with a latching function, respectively, which are complementary in form and size in order to establish a positive locking.

10. The orthotic system according to claim 9, wherein one of the elements of cuff and device comprises a retainer provided with one of the first part or second part of the positive locking system and the respective other element of cuff and device comprises an insertion element for positioning in the retainer, wherein the insertion element is provided with the respective other part of the first part or second part of the positive locking system and is designed to be pushed into the retainer along a slide-in direction, and due to an application of force, to bring the first part and second part in a positive locking.

11. The orthotic system according to claim 10, wherein the application of force is realized by an elastic behaviour of the insertion element pushing the respective first part or second part of the positive locking system in the direction of the respective first part or second part at the retainer in order to establish the positive locking, wherein the Young's modulus of the insertion element is between 0.5 GPa and 7 GPa.

12. The orthotic system according to claim 11, wherein a plurality of first parts and second parts of the positive locking system are arranged in rows, respectively, so that the positive locking can be realized at different positions along the slide-in direction.

13. The orthotic system according to claim 10, wherein the insertion element is adapted in such a way that the insertion element can be manually pushed and thus moved by a pressing force of at least 3 N so that its first part or second part of the positive locking system disengages from the positive locking with the respective first part or second part provided at the retainer.

14. The orthotic system according to claim 13, wherein a plurality of first parts and second parts of the positive locking system are arranged in rows, respectively, so that the positive locking can be realized at different positions along the slide-in direction.

15. The orthotic system according to claim 10, wherein a plurality of first parts and second parts of the positive locking system are arranged in rows, respectively, so that the positive locking can be realized at different positions along the slide-in direction.

* * * * *